(12) United States Patent
Boger

(10) Patent No.: US 7,351,724 B2
(45) Date of Patent: Apr. 1, 2008

(54) OXADIAZOLE KETONE INHIBITORS OF FATTY ACID AMIDE HYDROLASE

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/251,317

(22) Filed: Oct. 14, 2005

(65) Prior Publication Data
US 2006/0100212 A1 May 11, 2006

Related U.S. Application Data

(60) Provisional application No. 60/619,172, filed on Oct. 15, 2004.

(51) Int. Cl.
*A61K 31/4439* (2006.01)
*C07D 413/04* (2006.01)
(52) U.S. Cl. .................................. 514/340; 546/269.4
(58) Field of Classification Search ............ 546/269.4; 514/340
See application file for complete search history.

(56) References Cited

U.S. PATENT DOCUMENTS

| | | | |
|---|---|---|---|
| 4,518,601 A | 5/1985 | Kristiansen et al. | 514/340 |
| 6,462,054 B1 | 10/2002 | Boger | 514/302 |
| 6,891,043 B2 | 5/2005 | Boger | 546/115 |
| 2002/0103192 A1 | 8/2002 | Curtin et al. | 514/227.8 |

FOREIGN PATENT DOCUMENTS

| WO | WO 02/087569 A1 | 11/2002 |
|---|---|---|
| WO | WO 2004/033652 A2 | 4/2004 |

OTHER PUBLICATIONS

Edwards, et al., "Design, Synthesis, and Kinetic Evaluation of a Unique Class of Elastase Inhibitors, the Peptidyl a-Ketobenzoxazoles, and the X-ray Crystal Structure of the Covalent Complex between Porcine Pancreatic Elastase and Ac-Ala-Pro-Val-2-Benzoxazole", *J. Am. Chem. Soc. 114*: 1854-1863 (1992).
Devane, et al., "Isolation and Structure of a Brain Constituent That Binds to the Cannabinoid Receptor", *Science 258*: 1946-1949 (1992).
Lerner, et al., "Cerebrodiene: A Brain Lipid isolated from sleep-deprived cats", *Proc. Natl. Acad. Sci. USA 91*: 9505-9508 (1994).
Koutek, et al., "Inhibitors of Arachidonoyl Ethanolamide Hydrolysis", *J. Biol. Chem. 269*: 22937-22940 (1994).
Cravatt, et al., "Chemical Characterization of a Family of Brain Lipids That Induce Sleep", *Science 268*: 1506-1509 (1995).
Ueda, et al., "Partial Purification and Characterization of the Porcine Brain Enzyme Hydrolyzing and Synthesizing Anandamide", *J. Biol. Chem. 270*: 23823-23827 (1995).
Cravatt, et al., "Structure Determination of an Endogenous Sleep-Inducing Lipid, *cis*-9-Octadecenamide (Oleamide): A Synthetic Approach to the Chemical Analysis of Trace Quantities of a Natural Product", *J. Am. Chem. Soc. 118*: 580-590 (1996).
Patterson, et al., "Inhibition of Oleamide Hydrolase Catalyzed Hydrolysis of the Endogenous Sleep-Inducing Lipid *cis*-9-Octadecenamide", *J. Am. Chem. Soc. 118*: 5938-5945 (1996).
Cravatt, et al., "Molecular Characterization of an Enzyme that Degrades Neuromodulatory Fatty-Acid Amides", *Nature 384*: 83-87 (1996).
Petrocellis, et al., "Novel Inhibitors of Brain, Neuronal, and Basophilic Anandamide Amidohydrolase", *Biochem. Biophys. Res. Commun. 231*: 82-88 (1997).
Deutsch, et al., "Fatty Acid Sulfonyl Fluorides Inhibit Anandamide Metabolism and Bind to the Cannabinoid Receptor", *Biochem. Biophys. Res. Commun. 231*: 217-221 (1997).
Kurahashi, et al., "Reversible Hydrolysis and Synthesis of Anandamide Demonstrated by Recombinant Rat Fatty-Acid Amide Hydrolase", *Biochem. Biophys. Res. Commun. 237*: 512-515 (1997).
Bisogno, et al., "Biosynthesis Release and Degradation of the Novel Endogenous Cannabimimetic Metabolite-2-Arachidonoylglycerol in MouseNeuroblastoma Cells", *Biochem. J. 322*: 671-677 (1997).
Giang, et al., "Molecular Characterization of Human and Mouse Fatty Acid Amide Hydrolase", *Proc. Natl. Acad. Sci. USA 94*: 2238-2242 (1997).
Thomas, et al., "Fatty Acid Amide Hydrolase, the Degradative Enzyme for Anandamide and Oleamide, Has Selective Distribution in Neurons Within the Rat Central Nervous System", *J. Neuroscience Res. 50*: 1047-1052 (1997).
Di Marzo, et al., "The Novel Endogenous Cannabinoid 2-Arachidonoylglycerol is inactivated by neuronal- and basophil-like cells: connections with anandamide", *Biochem. J. 331*: 15-19 (1998).
Goparaju, et al., "Anandamide amidohydrolase reacting with 2-arachidonoylglycerol, another cannabinoid receptor ligand", *FEBS Lett. 422*: 69-73 (1998).
Murillo-Rodriguez, et al., "Anandamide modulates sleep and memory in rats", *Brain Res. 812*: 270-274 (1998).
Patricelli, et al., "An Endogenous Sleep-Inducing Compound is a Novel Competitive Inhibitor of Fatty Acid Amide Hydrolase", *Bioorg. Med. Chem. Lett. 8*: 613-618 (1998).
Boger, et al., "Structural Requirements for 5-HT$_{2A}$ and 5-HT$_{1A}$ Serotonin Receptor Potentiation by the Biologically Active Lipid Oleamide", *Proc. Natl. Acad. Sci. USA 95*: 4102-4107 (1998).
Maccarone, et al., "Anandamide Hydrolysis by Human Cells in Culture and Brain", *J. Biol. Chem. 273*: 32332-32339 (1998).
Boger, et al., "Trifluoromethyl Ketone Inhibitors of Fatty Acid Amide Hydrolase: A Probe of Structural and Conformational Features Contributing to Inhibition", *Bioorg. Med. Chem. Lett. 9*: 265-270 (1999).

(Continued)

*Primary Examiner*—Patricia L. Morris
(74) *Attorney, Agent, or Firm*—Donald G. Lewis

(57) ABSTRACT

Certain oxadiazole ketone compounds are useful as FAAH inhibitors. Such compounds may be used in pharmaceutical compositions and methods for the treatment of disease states, disorders, and conditions mediated by fatty acid amide hydrolase (FAAH) activity. Thus, the compounds may be administered to treat anxiety, pain, inflammation, sleep disorders, eating disorders, or movement disorders (such as MS).

8 Claims, No Drawings

OTHER PUBLICATIONS

Lang, et al., "Substrate Specificity and Stereoselectivity of Rat Brain Microsomal Anandamide Amidohydrolase", *J. Med. Chem. 42*: 896-902 (1999).

Boger, et al., "Exceptionally potent inhibitors of fatty acid amide hydrolase: The enzyme responsible for degradation of endogenous oleamide and anandamide", *Proc. Natl. Acad. Sci. USA 97*: 5044-5049 (2000).

Baker, et al., "Endocannabinoids control spasticity in a multiple sclerosis model", *FASEB J. 15*: 300-302 (2001).

Cravatt, et al., "Supersensitivity to anandamide and enhanced endogenous cannabinoid signaling in mice lacking fatty acid amide hydrolase", *Proc. Natl. Acad. Sci. USA 98*: 9371-9376 (2001).

Ueda, et al., "Purification and Characterization of an Acid Amidase Selective for N-Palmitoylethanolamine, a Putative Endogenous Anti-inflammatory Substance", *J. Biol. Chem. 276*: 35552-35557 (2001).

de Fonesca, et al., "An anorexic lipid mediator regulated by feeding", *Nature 414*: 209-212 (2001).

Mendelsen, et al., "The Hypnotic Actions of the Fatty Acid Amide, Oleamide", *Neuropsychopharmacology 25*: S36-S39 (2001).

Lambert, et al., "The Palmitoylethanolamide Family: A New Class of Anti-Inflammatory Agents?", *Curr. Med. Chem. 9*: 663-674 (2002).

Kathura, et al., "Modulation of anxiety through blockade of anandamide hydrolysis", *Nature Med 9*: 76-81 (2003).

Leung, et al., "Discovering potent and selective reversible inhibitors of enzymes in complex proteomes", *Nature Biotech. 21*: 687-691 (2003).

Piomelli, D., "The Molecular Logic of Endocannabinoid Signalling", *Nature Rev. 4*: 873-884 (2003).

OXADIAZOLE KETONE INHIBITORS OF FATTY ACID AMIDE HYDROLASE

This invention was made with United States Government support under Contract No. DA15648 by the National Institutes of Health. The United States Government has certain rights in the invention.

FIELD OF THE INVENTION

The present invention relates to certain oxadiazole ketone compounds, pharmaceutical compositions containing them, and methods of using them for the treatment of disease states, disorders, and conditions mediated by fatty acid amide hydrolase (FAAH) activity.

BACKGROUND OF THE INVENTION

Medicinal benefits have been attributed to the cannabis plant for centuries. The primary bioactive constituent of cannabis is $\Delta^9$-tetrahydrocannabinol (THC). The discovery of THC eventually led to the identification of two endogenous cannabinoid receptors responsible for its pharmacological actions, namely $CB_1$, and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4, 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9, 663).

Small molecule inhibitors of FAAH should elevate the concentrations of these endogenous signaling lipids and thereby produce their associated beneficial pharmacological effects. There have been some reports of the effects of various FAAH inhibitors in pre-clinical models.

Two carbamate-based inhibitors of FMH were reported to have analgesic properties in animal models. In rats, BMS-1 (WO 02/087569) was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9, 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15, 300).

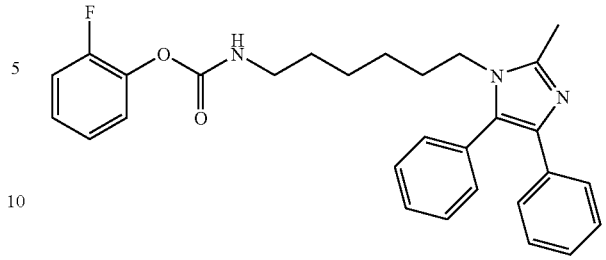

BMS-1

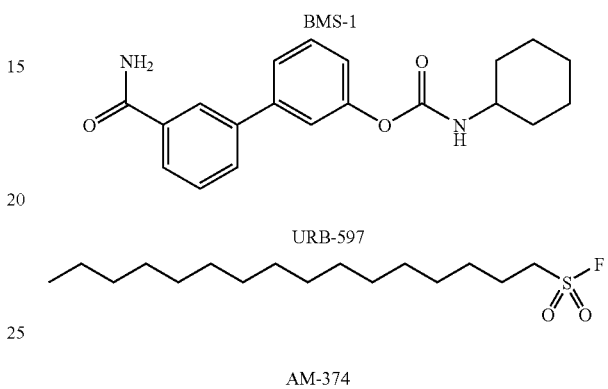

URB-597

AM-374

In addition, the oxazolopyridine ketone OL-135 is a potent inhibitor of FAAH, and has been reported to have analgesic activity in both the hot plate and tail emersion tests of thermal nociception in rats (WO 04/033652).

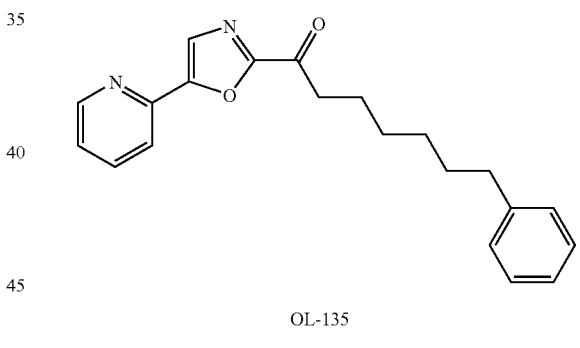

OL-135

Results of research on the effects of certain exogenous cannabinoids has elucidated that an FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDS who experience anorexia as a result of wasting syndrome. Two products are commercially available in some countries for these indications, namely, dronabinol (Marinol®) and nabilone.

Apart from the approved indications, the therapeutic field that has received the most attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain was initiated with CT-3 in Germany in May 2002.

Many individuals with multiple sclerosis have claimed a benefit from cannabis for both disease-related pain and spasticity, with support from small controlled trials (Svendsen, *Br. Med. J.* 2004, 329, 253). Likewise, victims of spinal cord injuries, such as paraplegia, have reported for years that their painful spasms are alleviated after smoking marijuana. Recently, a report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials are currently underway in multiple sclerosis and spinal cord injury patients with a narrow ratio mixture of tetrahydrocannabinol/cannabidiol (THC/CBD).

Small-scale controlled trials have been conducted to investigate other potential uses of cannabinoids. Trials in volunteers confirmed that oral, injected and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson, 2001).

Inhibition of FAAH using a small molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH –/– mice showed reduced responses in tests of nociception, but did not show catalepsy, hypothermia, or increased feeding behavior (Cravatt, *Proc. Nati. Acad. Sci. USA* 2001, 98, 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003).

In addition to the effects of an FAAH inhibitor on AEA and other endocannabinoids, inhibitors of FAAH's catabolism of other lipid mediators may be used in treating other therapeutic indications. For example, PEA has demonstrated biological effects in animal models of inflammation, immunosuppression, analgesia, and neuroprotection (Ueda, *J. Biol. Chem.* 2001, 276, 3552). Oleamide, another substrate of FAAH, induces sleep (Boger, *Proc. Natl. Acad. Sci. USA* 2000, 97, 5044; Mendelson, *Neuropsychopharmacology* 2001, 25, S36).

Thus, there is evidence that small-molecule FAAH inhibitors may be used in treating pain of various etiologies, anxiety, multiple sclerosis and other movement disorders, nausea/emesis, eating disorders, epilepsy, glaucoma, inflammation, immunosuppression, neuroprotection, and sleep disorders, and potentially with fewer side effects than treatment with an exogenous cannabinoid. There remains a need for potent FAAH modulators with desirable pharmaceutical properties.

SUMMARY OF THE INVENTION

Certain 2-keto-oxadiazole derivatives have now been found to have FMH-modulating activity.

In one general aspect, the invention relates to compounds of the following Formula (I)

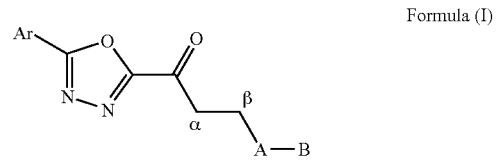

Formula (I)

wherein:

Ar is a 5- or 6-membered aryl or heteroaryl ring having a carbon as its point of attachment;

A is a straight-chain $C_{1-7}$alkylene having a carbon as its point of attachment to the carbon in the beta position shown above, which optionally has 1 or 2 carbon atoms replaced with an atom selected from sulfur, oxygen, and nitrogen;

B is a straight-chain, branched, or cyclic $C_{2-10}$alkyl, or is a moiety selected from the group consisting of aryl, $C_{2-10}$alkenyl, and $C_{2-10}$alkynyl, where an $sp^2$ or sp hybridized carbon atom in the aryl, alkenyl, or alkynyl is covalently attached to A;

or a pharmaceutically acceptable salt, pharmaceutically acceptable prodrug, or pharmaceutically active metabolite of such compound.

In a further general aspect, the invention relates to pharmaceutical compositions each comprising: (a) an effective amount of an agent selected from compounds of Formula (I) and pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition mediated by FAAH activity, comprising administering to the subject an effective amount of a compound of Formula (I) or a pharmaceutically acceptable salt, pharmaceutically acceptable prodrug, or pharmaceutically active metabolite of such compound.

In certain preferred embodiments of the method, the disease, disorder, or medical condition is selected from: anxiety, pain, sleep disorders, eating disorders, inflammation, multiple sclerosis and other movement disorders, HIV wasting syndrome, closed head injury, stroke, Alzheimer's disease, epilepsy, Tourette's syndrome, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, auto-immune diabetes, intractable pruritis, and neuroinflammation.

Additional embodiments, features, and advantages of the invention will be apparent from the appended claims, which are incorporated into this summary by reference, as well as from the following detailed description.

DETAILED DESCRIPTION AND PREFERRED EMBODIMENTS

The invention may be more fully appreciated by reference to the following description, including the following glossary of terms and the concluding examples. For the sake of brevity, the disclosures of the publications cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and the like.

The term "alkylene" refers to a divalent straight- or branched-chain alkyl group having from 1 to 12 carbon atoms in the chain. Exemplary alkylene groups include methylene, ethylene, propylene, and the like.

The term "alkenyl" refers to a straight- or branched-chain alkenyl group having from 2 to 12 carbon atoms in the chain. The double bond of the alkenyl group consists of two $sp^2$ hybridized carbon atoms. Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. The triple bond of the alkynyl group consists of two sp hybridized carbon atoms. Illustrative alkynyl groups include prop-2-ynyl, but-2-ynyl, but-3-ynyl, 2-methylbut-2-ynyl, hex-2-ynyl, and the like.

The term "aryl" refers to a monocyclic, fused bicyclic, or fused polycyclic, aromatic carbocycle (ring structure having ring atoms that are all carbon) having from 3 to 12 ring atoms per carbocycle. Carbon atoms in aryl groups are $sp^2$ hybridized. Illustrative examples of aryl groups include phenyl, naphthyl, anthracenyl, phenanthrenyl, and the like.

The term "heteroaryl" refers to a monocyclic, fused bicyclic, or fused polycyclic, aromatic heterocycle (ring structure having ring atoms selected from carbon atoms as well as nitrogen, oxygen, and sulfur heteroatoms) having from 3 to 12 ring atoms per heterocycle. Illustrative examples of heteroaryl groups include the following moieties:

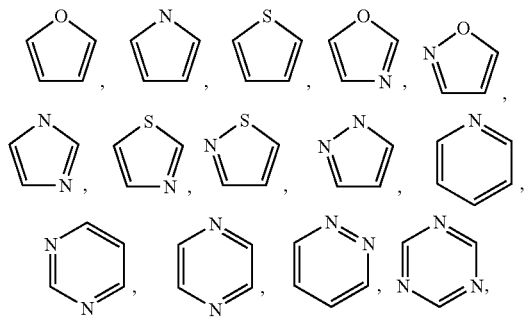

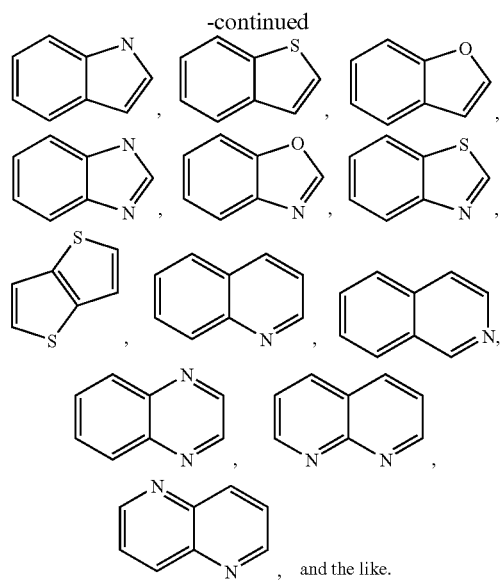

, and the like.

The term "cycloalkyl" refers to a saturated or partially saturated, monocyclic, fused polycyclic, or spiro polycyclic, carbocycle having from 3 to 12 ring atoms per carbocycle. Illustrative examples of cycloalkyl groups include the following moieties:

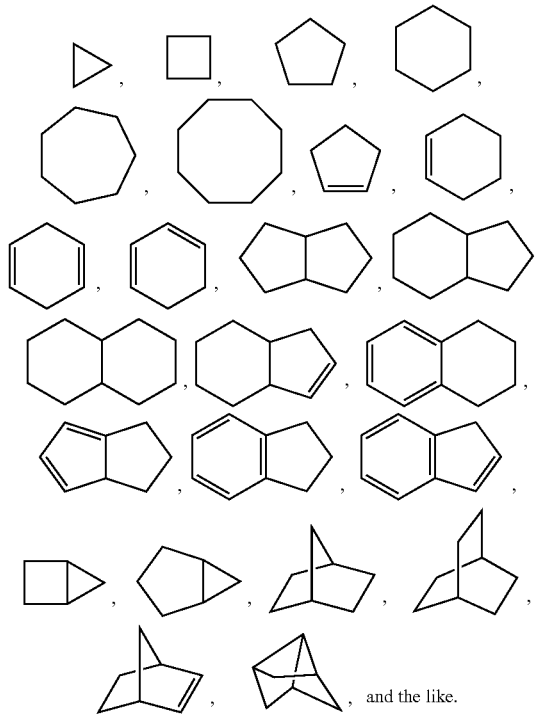

, and the like.

A "heterocycloalkyl" refers to a monocyclic, fused polycyclic, or spiro polycyclic, ring structure that is saturated or partially saturated and has from 3 to 12 ring atoms per ring structure selected from C atoms and N, O, and S heteroatoms. Illustrative examples of heterocycloalkyl groups include:

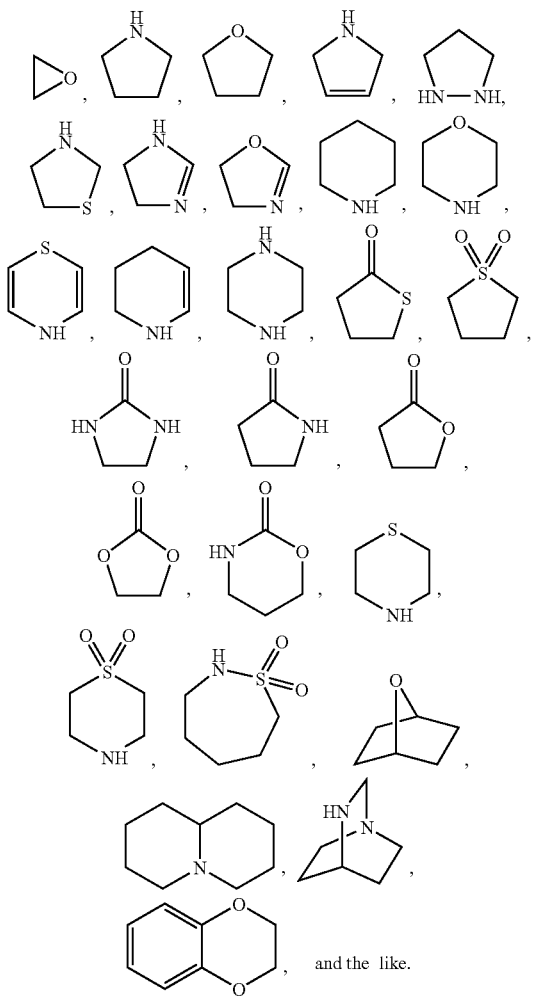

and the like.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In reference to Formula (I), the variable Ar represents a 5- or 6-membered aryl or heteroaryl ring, with the ring having a carbon atom as its point of attachment to the oxadiazole moiety shown in the formula. Preferably, Ar is selected from the group consisting of furanyl, pyridinyl, phenyl, pyridazinyl, pyrimidinyl, pyrazinyl, thiophenyl, oxazolyl, thiazolyl, oxadiazolyl, and isoxazolyl. More preferably, Ar is selected from the group consisting of phenyl, 2-pyridinyl, 3-pyridinyl, 4-pyridinyl, and furanyl.

The variable A in Formula (I) represents a straight-chain $C_{1-7}$alkylene. This aklylene moiety has a carbon as its point of attachment to the carbon in the beta position shown in the formula. Optionally, 1 or 2 carbon atoms of the alkylene may be replaced with a sulfur, oxygen, or nitrogen atom. Preferably, A is a straight-chain $C_{1-7}$alkylene, optionally having 1 or 2 carbon atoms replaced with oxygen. More preferably, A is a straight-chain $C_{1-7}$alkylene, without the optional replacement of any carbon atoms. Even more preferably, A is selected from the group consisting of propylene, butylene, pentylene, hexylene, propoxylene, butoxylene, and pentoxylene.

In general embodiments, the variable B in Formula (I) represents a straight-chain, branched, or cyclic $C_{2-10}$alkylene, or an aryl, $C_{2-10}$alkenyl, or $C_{2-10}$alkynyl group, with an $sp^2$ or sp hybridized carbon atom in the aryl, alkenyl, or alkynyl group covalently attached to variable A. In preferred embodiments, B is ethyl, propyl, isopropyl, butyl, sec-butyl, tert-butyl, phenyl, ethenyl, cis-1-decenyl, trans-1-decenyl, ethynyl, or 1-decynyl. More preferably, B is phenyl or cis-1-decenyl.

Preferred examples of compounds of the present invention are selected from the group consisting of:

EXAMPLE

Compound 1    7-Phenyl-1-[5-(pyridin-2-yl)-1,3,4-oxadiazol-2-yl]-heptan-1-one;
2    6-Phenyl-1-[5-(pyridin-2-yl)-1,3,4-oxadiazol-2-yl]-hexan-1-one;
3    8-Phenyl-1-[5-(pyridin-2-yl)-1,3,4-oxadiazol-2-yl]-octan-1-one;
4    9-Phenyl-1-[5-(pyridin-2-yl)-1,3,4-oxadiazol-2-yl]-nonan-1-one;
5    1-[5-(Pyridin-2-yl)-1,3,4-oxadiazol-2-yl]-octadec-9-en-1-one;
6    7-Phenyl-1-(5-phenyl-1,3,4-oxadiazol-2-yl )-heptan-1-one;
7    1-(5-Phenyl-1,3,4-oxadiazol-2-yl)-octadec-9-en-1-one;
8    6-Phenyl-1-[5-(pyridin-3-yl)-1,3,4-oxadiazol-2-yl]-hexan-1-one;
9    7-Phenyl-1-[5-(pyridin-3-yl)-1,3,4-oxadiazol-2-yl]-heptan-1-one;
10   7-Phenyl-1-[5-(pyridin-4-yl )-1,3,4-oxadiazol-2-yl]-heptan-1-one;
11   1-[5-(Furan-2-yl)-1,3,4-oxadiazol-2-yl]-heptan-1-one; and
12   6-Phenoxy-1-[5-(pyridin-2-yl)-[1,3,4]oxadiazol-2-yl]-hexan-1-one.

Any formula given herein is intended to represent compounds having structures depicted by the structural formula as well as certain variations or forms. In particular, compounds of any given formula given herein may have asymmetric centers and therefore exist in different enantiomeric forms. All optical isomers and stereoisomers of the compounds of the formula, and mixtures thereof, are considered within the scope of the formula. Thus, any given formula given herein is intended to represent a racemate, one or more enantiomeric forms, one or more diastereomeric forms, one or more atropisomeric forms, and mixtures thereof.

Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Various isotopically-labeled compounds of the present invention, for example those into which radioactive isotopes such as $^3H$, $^{11}C$, and $^{14}C$ are incorporated, are useful in drug or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The invention includes also pharmaceutically acceptable salts of the compounds represented by Formula (I). Pharmaceutically acceptable salts of the above-described specific compounds are especially preferred.

A "pharmaceutically acceptable salt" is intended to mean a salt of a free acid or base of a compound represented by Formula (I) that is not toxic, biologically intolerable, or otherwise biologically undesirable. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Exemplary pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, d initrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the compound of Formula (I) is a base, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid or ethanesulfonic acid, or the like.

If the compound of Formula (I) is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine and piperazine, and inorganic salts derived from sodium, calcium, potassium, magnesium, manganese, iron, copper, zinc, aluminum and lithium.

The invention also relates to treatment methods employing pharmaceutically acceptable prodrugs of the compounds represented by Formula (I). The term "prodrug" means a precursor of a compound of the specified formula that, following administration to a subject, yields the compound in vivo via a chemical or physiological process such as solvolysis or physiological conditions (e.g., a prodrug on being brought to physiological pH is converted to the compound of Formula (I)). A "pharmaceutically acceptable prodrug" is a prodrug that is not toxic, biologically intolerable, or otherwise biologically unsuitable for administration to the subject.

Exemplary prodrugs include compounds having an amino acid residue, or a polypeptide chain of two or more (e.g., two, three or four) amino acid residues, covalently joined through an amide or ester bond to a free amino, hydroxy or carboxylic acid group of a compound of Formula (I). Examples of amino acid residues include the twenty naturally occurring amino acids commonly designated by three letter symbols as well as 4-hydroxyproline, hydroxylysine, demosine, isodemosine, 3-methylhistidine, norvaline, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Exemplary amides include those derived from ammonia, primary $C_{1-6}$alkyl amines and secondary di($C_{1-6}$alkyl) amines. Secondary amines include 5- or 6-membered heterocycloalkyl or heteroaryl ring moieties having from 1 to 3 heteroatoms where at least one is a nitrogen atom. Preferred amides are derived from ammonia, $C_{1-3}$alkyl primary amines, and di($C_{1-2}$alkyl) amines. Exemplary esters of the invention include $C_{1-7}$alkyl, $C_{5-7}$carbocyclyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Advanced Drug Delivery Reviews*, 1996,19, 115. Carbamate derivatives of hydroxy and amino groups also yield prodrugs. Carbonate derivatives, sulfonate esters and sulfate esters of hydroxy groups also provide prodrugs. Derivatization of hydroxy groups as (acyloxy)methyl and (acyloxy)ethyl ethers, wherein the acyl group may be an alkyl ester, optionally substituted with one or more ether, amine or carboxylic acid functionalities, or where the acyl group is an amino acid ester as described above, are also encompassed. Prodrugs of this type may be prepared as described in J. Med. Chem. 1996, 39,10. Free amines can also be derivatized as amides, sulfonamides or phosphonamides. All of these prodrug moieties may incorporate groups including ether, amine and carboxylic acid functionalities.

Pharmaceutically active metabolites may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known in the art. See, e.g., Bertolini et al., *J. Med. Chem.* 1997, 40, 2011-2016; Shan et al., *J. Pharm. Sci.* 86 (7), 765-767; Bagshawe, *Drug Dev. Res.* 1995, 34, 220-230; Bodor, *Advances in Drug Res.* 1984, 13, 224-331; Bundgaard, Design of Prodrugs (Elsevier Press 1985); and Larsen, Design and Application of Prodrugs, Drug Design and Development (Krogsgaard-Larsen et al., eds., Harwood Academic Publishers, 1991).

The compounds represented by Formula (I) and their pharmaceutically acceptable salts, pharmaceutically acceptable prodrugs, and pharmaceutically active metabolites (collectively, "agents") of the present invention are useful as FAAH inhibitors in the methods of the invention. The agents may be used in the inventive methods for the treatment or prevention of medical conditions, diseases, or disorders mediated through inhibition or modulation of FAAH, such as those described herein. Agents according to the invention may therefore be used as an analgesic, neuroprotectant, sedative, appetite stimulant, or contraceptive.

Exemplary medical conditions, diseases, and disorders include anxiety, pain, sleep disorders, eating disorders, inflammation, multiple sclerosis and other movement disorders, HIV wasting syndrome, closed head injury, stroke, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, or cerebral vasospasm.

Thus, the pharmaceutical agents may be used to treat subjects diagnosed with or suffering from a disorder or condition mediated through FAAH activity. The term "treat" or "treating" as used herein is intended to refer to administration of an agent or composition of the invention to a subject for the purpose of effecting a therapeutic or prophylactic benefit through modulation of FAAH activity. Treating includes reversing, ameliorating, alleviating, inhibiting the progress of, lessening the severity of, or preventing a disease, disorder or condition, or one or more symptoms of such disease, disorder or condition. The term "subject" refers to a mammalian patient, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize or up-regulate FAAH expression or activity.

Accordingly, the invention relates to methods of using the pharmaceutical agents described herein, including those of the various preferred embodiments as well as those of the general embodiments, to treat subjects diagnosed with or suffering from a disorder or condition mediated through FAAH activity, such as: anxiety, pain, sleep disorders, eating disorders, inflammation, or movement disorders (e.g., multiple sclerosis).

Symptoms or disease states are intended to be included within the scope of "medical conditions, disorders, or diseases." For example, pain may be associated with various diseases and disorders, and may include various etiologies. Illustrative types of pain treatable with an FAAH-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In a treatment method according to the invention, an effective amount of a pharmaceutical agent according to the invention is administered to a patient suffering from or diagnosed as having such a disorder or condition. An "effective amount" means an amount or dose sufficient to generally bring about the desired therapeutic or prophylactic benefit in subjects in need of treatment.

Effective amounts or doses of the agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disorder or condition, the subject's previous or ongoing therapy, the subject's health status and response to drugs, and the judgment of the treating physician. An exemplary dose is in the range of from about 0.001 to about 200 mg of agent per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's conditions has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active compounds in the treatment of the above conditions. The additional compounds may be coadministered separately with an agent of Formula (I) or included with such an agent as an additional active ingredient in a pharmaceutical composition according to the invention. In an exemplary embodiment, additional active compounds are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The agents of the invention are used, alone or in combination with one or more other active ingredients, to formulate pharmaceutical compositions of the invention. A pharmaceutical composition of the invention comprises: (a) an effective amount of a pharmaceutical agent in accordance with the invention; and (b) a pharmaceutically acceptable excipient.

A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils and polyethylene glycols.

Delivery forms of the pharmaceutical compositions containing one or more dosage units of the pharmaceutical agents may be prepared using suitable pharmaceutical excipients and compounding techniques known to those skilled in the art. The compositions may be administered in the inventive methods by oral, parenteral, rectal, topical, or ocular routes or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol or water; preservatives (for example, methyl or propyl p-hydroxybenzoate or sorbic acid); wetting agents such as lecithin; and, if desired, flavoring or coloring agents.

The agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Exemplary agents useful in methods of the invention will now be described by reference to the illustrative synthetic schemes for their general preparation below and the specific examples that follow. Artisans will recognize that, to obtain the various compounds herein, starting materials may be employed that carry the ultimately desired substituents though the reaction scheme with or without protection as appropriate to yield the desired product. Alternatively, it may be necessary to employ, in the place of the ultimately desired substituent, a suitable group that may be carried through the reaction scheme and replaced as appropriate with the desired substituent. Unless otherwise specified, the variables are as defined above in reference to Formula (I).

SCHEME A

Referring to Scheme A, aryl hydrazides of formula (II) may be commercially available, or may be prepared by addition of hydrazine to an aryl acid chloride. Aryl hydrazides may then be treated with methyl oxalyl chloride to form acylhydrazides of formula (III). Treatment of compounds of formula (III) with a dehydrating agent such as p-toluenesulfonyl chloride results in cyclization to the oxadiazole esters of formula (IV). These esters may be treated with a nucleophile such as an alkyl Grignard or alkyllithium reagent to form the FAAH inhibitors of Formula (I). Generally, the nucleophiles can be obtained from the corresponding halide by treatment with Mg metal or an alkyl lithium reagent.

SCHEME B

Referring to alternative Scheme B, compounds of Formula (I) can be obtained by treatment of an appropriate aryloxadiazole of formula (V) with an alkyllithium reagent, followed by transmetalation with zinc and copper using the method of Anderson (*Tetrahedron Lett*. 1995, 36, 9453-9456), to form the corresponding cuprate. The cuprate prepared from (V) may be coupled with an appropriate acid chloride of formula (VI) to provide FAAH inhibitors of Formula (I).

The following specific examples are provided to further illustrate the invention.

EXAMPLES

Experimental

NMR spectra were obtained on either a Bruker model AMX400 (400 MHz) or DRX500 (500 MHz) spectrometer. The format of the $^1$H NMR data below is: chemical shift in ppm down field of the tetramethylsilane reference (multiplicity, coupling constant J in Hz, integration).

Mass spectra were obtained on an Agilent series 1100 MSD using electrospray ionization (ESI) or Varian VGZAB-VSE or VG 70-VSE MS using FAB or MALDI ionization in either positive or negative mode as indicated. The "mass calculated" for a molecular formula is the monoisotopic mass of the compound.

Example 1

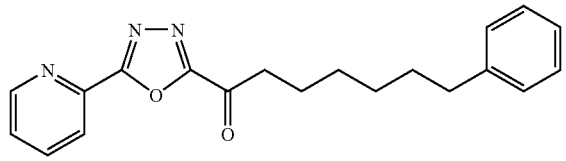

7-Phenyl-1-[5-(pyridin-2-yl)-1,3,4-oxadiazol-2-yl]-heptan-1-one

Step A: Methyl 5-(Pyridin-2-yl)-[1,3,4]-oxadiazole-2-carboxylate.

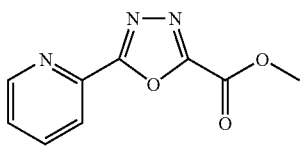

2-Picolinyl hydrazide (1.37 g, 10 mmol) and Et$_3$N (4.15 mL, 30 mmol) were dissolved in CH$_2$Cl$_2$ (50 mL) and treated with methyl oxalyl chloride (0.95 mL, 10 mmol) dropwise at 0° C. The reaction mixture was slowly warmed to room temperature and stirred for 6 h before it was treated with p-toluenesulfonyl chloride (TsCl; 1.91 g, 10 mmol) and stirred overnight. The reaction mixture was diluted with EtOAc and washed with water, satd. aq. NaHCO$_3$ and brine. The organic layer was collected and concentrated. Flash chromatography (SiO$_2$, 3×15 cm, 70% EtOAc-hexanes) afforded the title compound (1.87 g, 91%) as white solid. $^1$H NMR (400 MHz, CDCl$_3$) 4.07 (s, 3H), 7.52 (ddd, J=7.8, 4.9, 1.2 Hz, 1H), 7.92 (td, J=7.8, 1.8 Hz, 1H), 8.29 (d, J=7.9 Hz, 1H), 8.80 (dd, J=4.2, 1.2 Hz, 1H); $^{13}$C NMR (CDCl$_3$, 100 MHz) 53.8, 123.8, 126.7, 137.3, 142.3, 150.6, 154.4, 156.8, 165.2.

Step B: 7-Phenyl-1-[5-(pyridin-2-yl)-1,3,4-oxadiazol-2-yl]-heptan-1-one. A dry flask was charged with freshly activated Mg turnings (115 mg, 5 mmol), 100 μL of anhydrous THF and a crystal of $I_2$ under Ar. This mixture was treated dropwise with a solution of 6-bromohexylbenzene (240 mg, 1 mmol) in THF (1 mL) at 60° C. After the addition was complete, the mixture was stirred for 2 h at 60° C. The resulting gray solution of the Grignard reagent was added to a solution of the oxadiazole methyl ester from Step A (40 mg, 0.17 mmol) in THF (2 mL) at −40° C. Stirring was continued for 4 h before the reaction was quenched with the addition of brine. The mixture was extracted with EtOAc followed by separation and concentration. Flash chromatography ($SiO_2$, 1×4 cm, 40% EtOAc-hexanes) afforded the title compound (30 mg, 51%) as white solid. $^1$H NMR (400 MHz, $CDCl_3$) 1.43 (m, 4H), 1.66 (quintet, J=7.5 Hz, 2H), 1.82 (quintet, J=7.3 Hz, 2H), 2.62 (dd, J=7.9, 7.6 Hz, 2H), 3.31 J=7.3 Hz, 2H), 7.16-7.19 (m, 3H), 7.26-7.30 (m, 2H), 7.54 (ddd, J=7.6, 4.7, 0.9 Hz, 1H), 7.93 (td, J=7.8, 1.5 Hz, 1H), 8.30 (d, J=7.9 Hz, 1H), 8.85 (d, J=4.7 Hz 1H); $^{13}$C NMR ($CDCl_3$, 100 MHz) 23.5, 28.8, 28.9, 31.2, 35.8, 40.0, 124.0, 125.6, 126.7, 128.2, 128.3, 137.3, 142.6, 150.8, 161.2, 165.0, 187.1; MALDI-FTMS m/z 336.1717 ($C_{20}H_{21}N_3O_2+H^+$ requires 336.1706).

Example 2

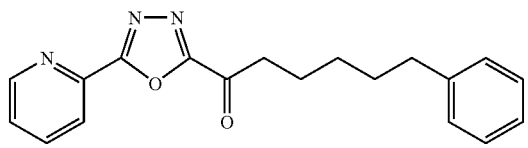

6-Phenyl-1-[5-(pyridin-2-yl)-1,3,4-oxadiazol-2-yl]-hexan-1-one

Starting with methyl 5-(pyridin-2-yl)-[1,3,4]-oxadiazole-2-carboxylate and 5-bromopentylbenzene, the title compound (21 mg, 49%) was obtained as a white solid, using a procedure similar to Example 1. $^1$H NMR (400 MHz, $CDCl_3$) 1.45 (m, 2H), 1.68 (quintet, J=7.8 Hz, 2H), 1.86 (quintet, J=7.6 Hz, 2H), 2.62 (t, J=7.6 2H), 3.31 (t, J=7.5 Hz, 2H), 7.18-7.20 (m, 3H), 7.27-7.29 (m, 2H), 7.54 (d 7.9, 5.0, 1.2 Hz, 1H), 7.94 (td, J=7.6, 1.8 Hz, 1H), 8.30 (d, J=7.9 Hz, 1H), 8.85 (d, J=5.0 Hz, 1H); $^{13}$C NMR ($CDCl_3$, 100 MHz) 23.4, 28.6, 31.1, 35.7, 40.0, 124.0, 125.7, 126.7, 128.3, 128.4, 137.3, 142.3, 142.6, 150.8, 161.2, 165.1, 187.0; MALDI-FTMS m/z 322.1557 ($C_{19}H_{19}N_3O_2+H^+$ requires 322.1556).

Example 3

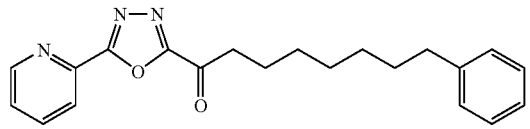

8-Phenyl-1-[5-(pyridin-2-yl)-1,3,4-oxadiazol-2-yl]-octan-1-one

Starting with methyl 5-(pyridin-2-yl)-[1,3,4]-oxadiazole-2-carboxylate and 7-bromoheptylbenzene, the title compound (25 mg, 41%) was obtained as a white solid, using a procedure similar to Example 1. $^1$H NMR (400 MHz, $CDCl_3$) 1.38 (m, 6H), 1.63 (quintet, J=7.3 Hz, 2H), 1.80 (quintet, J=7.0 Hz, 2H), 2.61 (dd, J=7.9, 7.6 Hz, 2H), 3.21 (t, J=7.5 Hz, 2H), 7.16-7.19 (m, 3H), 7.26-7.30 (m, 2H), 7.54 (ddd, J=7.6, 4.7, 0.9 Hz, 1H), 7.94 (td, J=7.8,1.8 Hz, 1H), 8.30 (d, J=7.9 Hz, 1H), 8.85 (d, J=4.7 Hz, 1H); $^{13}$C NMR ($CDCl_3$, 100 MHz) 23.6, 28.9, 29.0, 29.1, 31.4, 35.7, 35.9, 40.1, 124.0, 125.6, 126.7, 128.2, 128.4, 137.3, 142.6, 142.7, 150.8, 161.2, 165.1, 187.2; MALDI-FTMS m/z 350.1859 ($C_{21}H_{23}N_3O_2+H^+$ requires 350.1863).

Example 4

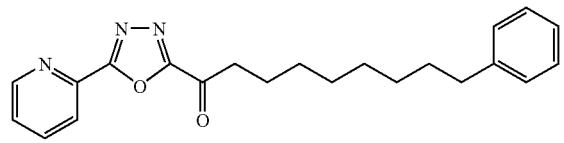

9-Phenyl-1-[5-(pyridin-2-yl)-1,3,4-oxadiazol-2-yl]-nonan-1-one

Starting with methyl 5-(pyridin-2-yl)-[1,3,4]-oxadiazole-2-carboxylate and 8-bromooctylbenzene, the title compound (28 mg, 43%) was obtained as a white solid using a procedure similar to Example 1. $^1$H NMR (400 MHz, $CDCl_3$) 1.34 (m, 8H), 1.62 (quintet, J=7.3 Hz, 2H), 1.81 (quintet, J=7.3 Hz, 2H), 2.61 (dd, J=7.9, 7.6 Hz, 2H), 3.21 (t, J=7.5 Hz, 2H), 7.16-7.19 (m, 3H), 7.26-7.30 (m, 2H), 7.54 (dd, J=7.6, 4.7, Hz, 1H), 7.93 (td, J=7.6, 1.5 Hz, 1H), 8.30 (d, J=7.9 Hz, 1H), 8.85 (d, J=4.7 Hz, 1H); $^{13}$C NMR ($CDCl_3$, 100 MHz) 23.6, 28.9, 29.00, 29.02, 29.2, 31.4, 35.90, 35.92, 40.1, 124.0, 125.5, 126.7, 128.2, 128.4, 137.3, 142.6, 142.8, 150.8, 161.2, 165.0, 187.2; MALDI-FTMS m/z 364.2024 ($C_{22}H_{25}N_3O_2+H^+$ requires 364.2019).

Example 5

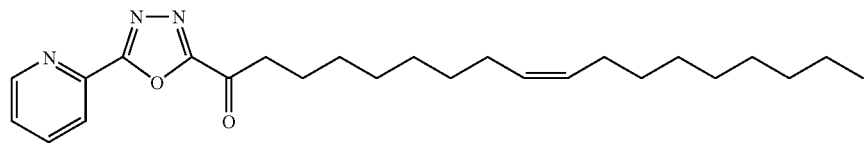

1-[5-(Pyridin-2-yl)-1,3,4-oxadiazol-2-yl]-octadec-9-en-1-one

A solution of cis-1-bromo-heptadec-8-ene (60 mg, 0.2 mmol) in THF (1 mL) was treated with t-BuLi (1.5 M in pentane, 270 μL, 0.4 mmol) at −40° C. After stirring for 30 min, the resulting alkyl lithium reagent was added to a solution of methyl 5-(pyridin-2-yl)-[1,3,4]-oxadiazole-2-carboxylate (20 mg, 0.1 mmol) in THF (2 mL) at −40° C. The reaction mixture was stirred for 4 h before it was quenched with the addition of brine. The mixture was extracted with EtOAc, concentrated, and purified by flash chromatography (SiO$_2$, 1×3 cm, 30% EtOAc-hexanes) to provide the title compound (8.5 mg, 23%) as white solid. $^1$H NMR (400 MHz, CDCl$_3$) 8.85 (dd, J=5, 1.2 Hz, 1H), 8.30 (dd, J=7.9, 1.2 Hz, 1H), 7.94 (td, J=7.6, 1.5 Hz, 1H), 7.54 (ddd, J=7.6, 4.7, 1.2 Hz, 1H), 5.34-5.37 (m, 2H), 3.22 (t, J=7.3 Hz, 2H), 2.02 (m, 4H), 1.82 (m, 2H), 1.27-1.41 (m, 20H), 0.88 (t, J=6.4 Hz, 3H); $^{13}$C NMR (CDCl$_3$, 100 MHz) 187.2, 165.1, 161.2, 150.8, 142.6, 150.8, 142.6, 137.3, 130.0, 129.7, 126.7, 124.0, 40.1, 31.9, 29.8, 29.7, 29.5, 29.3, 29.2, 29.1, 29.0, 27.2, 27.1, 23.6, 22.7, 14.1; MALDI-FTMS m/z 412.2955 (C$_{25}$H$_{37}$N$_3$O$_2$+H$^+$ requires 412.2958).

Example 6

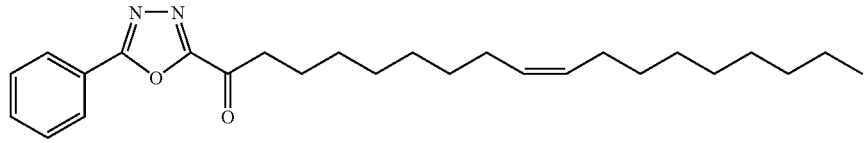

7-Phenyl-1-(5-phenyl-1,3,4-oxadiazol-2-yl)-heptan-1-one

Step A: Methyl 5-Phenyl-1,3,4-oxadiazole-2-carboxylate.

Starting with benzoyl hydrazide, the title compound (1.93 g, 94%) was obtained as a white solid, using a method analogous to that described in Example 1, Step A. $^1$H NMR (400 MHz, CDCl$_3$) 4.05 (s, 3H), 7.48-7.59 (m, 3H), 8.11 (m, 2H); $^{13}$C NMR (CDCl$_3$, 100 MHz) 53.7, 122.5, 127.4, 129.1, 132.7, 154.6, 156.1, 166.3; MALDI-FTMS m/z 205.0602 (C$_9$H$_8$N$_2$O$_3$+H$^+$ requires 205.0608).

Step B: 7-Phenyl-1-(5-phenyl-1,3,4-oxadiazol-2-yl)-heptan-1-one. Starting with methyl 5-phenyl-1,3,4-oxadiazole-2-carboxylate, the title compound (32 mg, 49%) was obtained as white solid, using a method analogous to that described in Example 1, Step B. $^1$H NMR (400 MHz, CDCl$_3$) 1.44 (m, 4H), 1.66 (quintet, J=7.4 Hz, 2H), 1.82 (quintet, J=7.3 Hz, 2H), 2.63 (dd, J=7.9, 7.4 Hz, 2H), 3.20 (t, J=7.3 Hz, 2H), 7.16-7.20 (m, 3H), 7.26-7.30 (m, 2H), 7.54-7.62 (m, 3H), 8.17-8.20 (m, 2H); $^{13}$C NMR (CDCl$_3$, 100 MHz) 23.6, 28.8, 28.9, 31.2, 35.8, 35.9, 39.8, 122.8, 125.6, 127.7, 128.2, 128.4, 129.2, 132.9, 142.6, 160.8, 166.3, 187.5; MALDI-FTMS m/z 335.1758 (C$_{21}$H$_{22}$N$_2$O$_2$+H$^+$ requires 335.1754).

Example 7

1-(5-Phenyl-1,3,4-oxadiazol-2-yl)-octadec, 9-en-1-one

A solution of 2-phenyl-[1,3,4]-oxadiazole (73 mg, 0.5 mmol) in THF (5 mL) was treated with 2.5 M BuLi (240 μL, 0.6 mmol) at −78° C. After stirring for 30 min, ZnCl$_2$ (1 M in diethyl ether, 1 mL, 1 mmol) was added. The reaction mixture was warmed to 0° C. and stirred for 45 min before CuI (100 mg, 0.5 mmol) was added. After stirring for 15 min, the reaction mixture was treated with a solution of oleoyl chloride (400 μL, 1 mmol) in THF (2 mL) and reaction mixture was stirred for 5 h before it was quenched with the addition of brine. The mixture was extracted with EtOAc, concentrated, and purified by flash chromatography (SiO$_2$, 1×3 cm, 20% EtOAc-hexanes) to provide the title compound (40 mg, 20%) as thick oil. $^1$H NMR (400 MHz, CDCl$_3$) 8.18 (dd, J=7, 1.5 Hz, 2H), 7.61 (m, 1H), 7.55 (m, 2H), 5.34-5.39 (m, 2H), 3.20 (t, J=7.4 Hz, 2H), 2.01 (m, 4H), 1.81 (quintet, J=7.4 Hz, 2H), 1.27-1.42 (m, 20H), 0.88 (t, J=7.0 Hz, 3H); $^{13}$C NMR (CDCl$_3$, 100 MHz) 187.6 160.9, 132.8, 130.0, 129.7, 129.2, 127.8, 122.8, 39.9, 31.9, 29.8, 29.7, 29.5, 29.3, 29.2, 29.1, 27.2, 27.1, 23.7, 22.7, 14.1; MALDI-FTMS m/z 411.3010 (C$_{26}$H$_{38}$N$_2$O$_2$+H$^+$ requires 411.3006).

Example 8

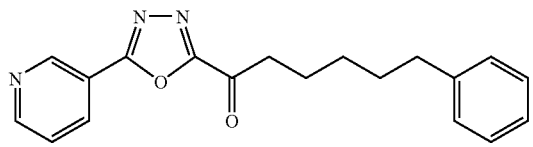

6-Phenyl-1-[5-(pyridin-3-yl)-1,3,4-oxadiazol-2-yl]-hexan-1-one

Step A: Methyl 5-(pyridin-3-yl)-1,3,4-oxadiazole-2-carboxylate.

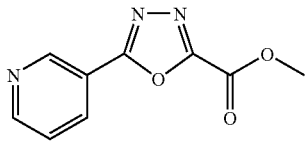

Starting with 3-picolinyl hydrazide, the title compound (1.53 g, 75%) was obtained as a white solid, using a method analogous to that described in Example 1, Step A. $^1$H NMR (500 MHz, CDCl$_3$) 4.11 (s, 3H), 7.52 (ddd, J=8.1, 4.8, 1.1 Hz, 1H), 8.46 (dt, J=8.1, 2.0 Hz, 1H), 8.85 (dd, J=5.2, 1.6 Hz, 1H), 9.39 (d, J=2.2 Hz, 1H); $^{13}$C NMR (CDCl$_3$, 100 MHz) 53.9, 119.3, 123.9, 134.7, 148.4, 153.4, 154.5, 156.6, 164.4; MALDI-FTMS m/z 206.0560 (C$_9$H$_7$N$_3$O$_3$+H$^+$ requires 206.056).

Step B: 6-Phenyl-1-[5-(pyridin-3-yl)-1,3,4-oxadiazol-2-yl]-hexan-1-one. By using procedure analogous to that described in Example 1, Step B, the title compound was prepared (42 mg, 73%) as white solid. $^1$H NMR (400 MHz, CDCl$_3$) 1.48 (m, 2H), 1.70 (quintet, J=7.6 Hz, 2H), 1.85 (quintet, J=7.6 Hz, 2H), 2.64 (t, J=7.8 Hz, 2H), 3.21 (t, J=7.5 Hz, 2H), 7.16-7.19 (m, 3H), 7.26-7.30 (m, 2H), 7.52 (ddd, J=5.0, 0.9 Hz, 1H), 8.45 (dt, J=7.9, 2.0 Hz, 1H), 8.85 (dd, J=4.7, 1.8 Hz, 1H), 9.41 (d, J=2 Hz, 1H); $^{13}$C NMR (CDCl$_3$, 100 MHz) 23.5, 28.5, 31.0, 35.6, 39.9, 119.4, 123.9, 125.7, 128.2, 128.3, 134.8, 142.3, 148.6, 153.4, 161.0, 164.2, 187.2; MALDI-FTMS m/z 322.1540 (C$_{19}$H$_{19}$N$_3$O$_2$+H$^+$ requires 322.155).

Example 9

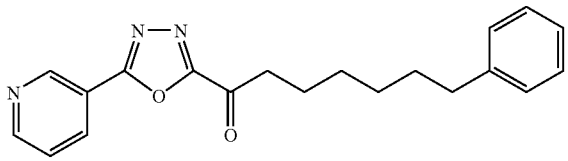

7-Phenyl-1-[5-(pyridin-3-yl)-1,3,4-oxadiazol-2-yl]-heptan-1-one

Starting with methyl 5-(pyridin-3-yl)-[1,3,4]-oxadiazole-2-carboxylate and 6-bromohexylbenzene, the title compound (20 mg, 34%) was obtained as a white solid, using a procedure analogous to that described in Example 1. $^1$H NMR (400 MHz, CDCl$_3$) 1.44 (m, 4H), 1.66 (quintet, J=7.5 Hz, 2H), 1.82 (quintet, J=7.3 Hz, 2H), 2.63 (dd, J=7.9, 7.3 Hz, 2H), 3.21 (t, J=7.4 Hz, 2H), 7.17-7.19 (m, 3H), 7.26-7.30 (m, 2H), 7.52 (ddd, J=7.9, 4.7, 0.6 Hz, 1H), 7.94 (dt, J=7.9, 1.9 Hz, 1H) 8.85 (dd, J=5.0, 1.8 Hz, 1H), 9.41 (d, J=1.8 Hz, 1H); $^{13}$C NMR (CDCl$_3$, 100 MHz) 23.6, 28.8, 28.9, 31.2, 35.9, 40.0, 119.4, 123.9, 125.6, 128.2, 128.4, 134.9, 142.3, 148.7, 153.4, 161.0, 164.3, 187.3; MALDI-FTMS m/z 336.1716 (C$_{20}$H$_{21}$N$_3$O$_2$+H$^+$ requires 336.1706).

Example 10

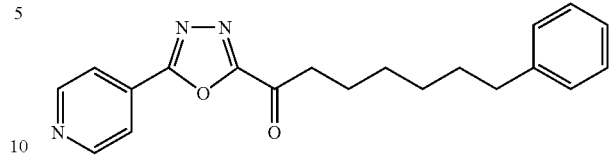

7-Phenyl-1-[5-(pyridin-4-yl)-1,3,4-oxadiazol-2-yl]-heptan-1-one

Starting with 4-picolinyl hydrazide and 6-bromohexylbenzene, the title compound (25 mg, 42%) was obtained as a white solid, using a procedure analogous to that described in Example 1. $^1$H NMR (500 MHz, CDCl$_3$) 1.44 (m, 4H), 1.66 (quintet, J=7.6 Hz, 2H), 1.82 (quintet, J=7.4 Hz, 2H), 2.63 (t, J=7.7 Hz, 2H), 3.21 (t, J=7.5 Hz, 2H), 7.17-7.19 (m, 3H), 7.26-7.30 (m, 2H), 8.03 (dd, J=4.4, 1.5 Hz, 2H), 8.88 (dd, J=4.4, 1.5 Hz, 2H); $^{13}$C NMR (CDCl$_3$, 100 MHz) 23.5, 28.8, 28.9, 31.2, 35.8, 40.0, 120.8, 125.6, 128.3, 128.4, 129.9, 142.5, 151.1, 161.1, 164.4, 187.2; MALDI-FTMS m/z 336.1715 (C$_{20}$H$_{21}$N$_3$O$_2$+H$^+$ requires 336.1706).

Example 11

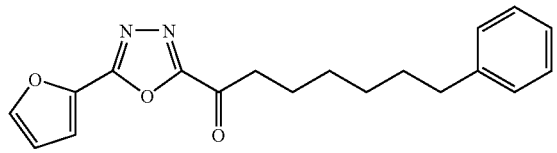

1-[5-(Furan-2-yl)-1, 3,4-oxadiazol-2-yl]-heptan-1-one

Starting with 2-furanyl hydrazide and 6-bromohexylbenzene, the title compound (47 mg, 57%) was obtained as a white solid, using a procedure analogous to that described in Example 1. $^1$H NMR (400 MHz, CDCl$_3$) 1.43 (m, 4H), 1.65 (quintet, J=7.3 Hz, 2H), 1.81 (quintet, J=7.3 Hz, 2H), 2.62 (dd, J=7.9, 7.5 Hz, 2H), 3.18 (t, J=7.3 Hz, 2H), 6.66 (ddd, J=3.5, 1.8, 0.9 Hz, 1H), 7.18-7.19 (m, 3H), 7.26-7.30 (m, 2H), 7.36 (dd, J=3.8, 0.9 Hz, 1H), 7.72 (dd, J=1.8, 0.9 Hz, 1 H) $^{13}$C NMR (CDCl$_3$, 100 MHz) 23.6, 28.8, 28.9, 31.2, 35.6, 39.9, 112.6, 116.6, 125.6, 128.2, 128.3, 138.5, 142.5, 147.0, 158.7, 159.9, 187.1.

Example 12

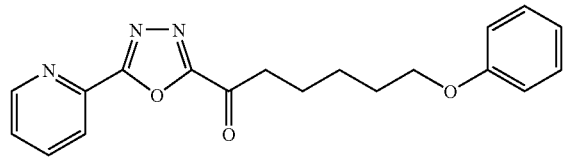

6-Phenoxy-1-(5-pyridin-2-yl-[1,3,4]oxadiazol-2-yl)-hexan-1-one

The title compound is prepared using a method analogous to those described above in Examples 1-11.

Assay Method

All enzyme assays were performed at 20-23° C. using a solubilized liver plasma membrane extract containing FMH in a reaction buffer of 125 mM Tris, 1 mM EDTA, 0.2% glycerol, 0.02% Triton X-100, 0.4 mM HEPES, pH 9.0 buffer (Patricelli, M. P. et al. *Bioorg. Med. Chem. Lett.* 1998, 8, 613-618; Patterson, J. E., et al. *J. Am Chem. Soc.* 1996, 118, 5938-5945). The initial rates of hydrolysis were monitored by following the breakdown of $^{14}C$-oleamide to oleic acid as described previously (Cravatt, B. F. et al. *Science* 1995, 268, 1506-1509; Patricelli, M. P. et al., 1998). The inhibition was reversible, non time-dependent. Linear least squares fits were used for all reaction progress curves and $R^2$ values were consistently >0.97. $IC_{50}$ values were determined from the inhibition observed at 3-5 different test compound concentrations (from three or more trials at each concentration) using the formula $IC_{50}=[I]/[(K_0/K_i)-1]$, where $K_0$ is the control reaction rate without inhibitor and $K_i$ is the rate with test compound at concentration [I] (Conde-Frieboes, K., et al. *J. Am. Chem. Soc.* 1996, 118, 5519-5525). $K_i$ values were determined by the Dixon Method (x-intercepts of weighted linear fits of [I] versus 1/rate plots at constant substrate concentration, which were converted to $K_i$ values using the formula $K_i=-x_{int}/[1+[S]/K_m]$). Data for the identified examples are presented in Table 1.

TABLE 1

| Ex. | $K_i$ (nM) |
|---|---|
| 1 | 0.29 |
| 2 | 0.85 |
| 3 | 0.77 |
| 4 | 0.83 |
| 5 | 3.0 |
| 6 | 2.0 |
| 7 | 16 |
| 8 | ND |
| 9 | 1.0 |
| 10 | 1.0 |
| 11 | 0.56 |

ND = not determined

Selectivity Assay

Serine hydrolases represent one of the largest classes of enzymes collectively comprising approximately 3% of the predicted Drosophila proteome. Subclasses include serine proteases, lipases, esterases, amidases, and transacetylases. To date, designed FAAH inhibitors have not demonstrated competitive inhibition with respect to other serine hydrolases. Disclosed herein is the use of a proteome-wide serine hydrolase screen (Kidd, D., et al., *Biochemistry* 2001, 40, 4005-4015; Liu, Y., et al., *Proc. Natl. Acad. Sci. USA* 1999, 96, 14694-14699) adapted to assay the selectivity of FAAH inhibitors (Leung, D., et al., *Nature Biotech.* 2003, 21, 687-691).

Biotinylated (B) or fluorescently-tagged (rhodamine, R) PEG-fluorophosphonate (BPFP or RPFP, respectively) have been used to isolate and identify (BPFP) or quantitate (RPFP) proteome serine hydrolases through selective, irreversible active site labeling (Kidd, D., et al., 2001; Liu, Y., et al., 1999). Extending this to the assessment of inhibitor selectivity required incubation of the proteome with RPFP in the presence of systematically varied concentrations of inhibitor followed by SDS-PAGE to detect serine hydrolases sensitive to the inhibitor (Leung, D., et al., 2003). A resulting inhibition of RPFP active site labeling correlated with inhibitor affinity for the target and permitted the simultaneous assessment of competitive enzymes. Significantly, the selectivity screening did not require the use of a competitive substrate, no modification of the inhibitor was required, and the results were rapidly quantitated ($IC_{50}$'s).

Two enzymes emerged from the screen as competitive targets for the oxadiazole ketone compounds detailed herein: triacylglycerol hydrolase (TGH) and an uncharacterized membrane-bound hydrolase that lacks known substrates and function (KIAA1363) (Kidd, D., et al., 2001; Liu, Y., et al., 1999; Leung, D., et al., 2003). The results of the selectivity screen are shown in Table 2.

TABLE 2

| Ex. | FAAH $K_i$ (nM) | FAAH $IC_{50}$ (nM) | KIAA $IC_{50}$ (nM) | TGH $IC_{50}$ (nM) |
|---|---|---|---|---|
| 1 | 0.29 | 1 | $5 \times 10^4$ | 140 |
| 2 | 0.85 | 4 | $9 \times 10^4$ | 30 |
| 3 | 0.77 | 0.6 | $6 \times 10^4$ | 200 |
| 4 | 0.83 | 0.8 | $3 \times 10^3$ | 500 |
| 6 | 2.0 | 25 | $>1 \times 10^5$ | 250 |
| 9 | 1.0 | 20 | $>1 \times 10^5$ | 100 |
| 10 | 1.0 | 20 | $>1 \times 10^5$ | 30 |
| 11 | 0.56 | 1 | $>1 \times 10^5$ | 80 |

While the invention has been illustrated by reference to exemplary and preferred embodiments, it will be understood that the invention is intended not to be limited to the foregoing detailed description, but to be defined by the appended claims as properly construed under principles of patent law.

What is claimed is:

1. A compound of Formula (I):

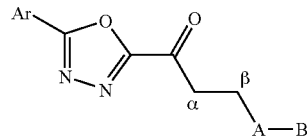

wherein:
Ar is a pyridinyl ring having a carbon as its point of attachment;
A is a straight-chain $C_{1-7}$alkylene having a carbon as its point of attachment to the carbon in the beta position, optionally having 1 or 2 carbon atoms each replaced with a sulfur, oxygen, or nitrogen atom;
B is a straight-chain, branched, or cyclic $C_{2-10}$alkylene, or, is an aryl, $C_{2-10}$alkenyl, or $C_{2-10}$alkynyl, where an $sp^2$ hybridized carbon atom in said aryl, alkenyl, or alkynyl is covalently attached to A;
or a pharmaceutically acceptable salt of said compound.

2. A compound as defined in claim 1, wherein A is a straight-chain $C_{1-7}$alkylene, optionally having 1 or 2 carbon atoms each replaced with an oxygen atom.

3. A compound as defined in claim 2, wherein B is selected from the group consisting of ethyl, propyl, isopropyl, butyl, sec-butyl, tert-butyl, phenyl, ethenyl, cis-b 1-decenyl, trans-1-decenyl, ethynyl, and 1-decynyl.

4. A compound as defined in claim 1, wherein B is selected from the group consisting of ethyl, propyl, isopropyl, butyl, sec-butyl, tert-butyl, phenyl, ethenyl, cis-1-decenyl, trans-1-decenyl, ethynyl, and 1-decynyl.

5. A compound as defined in claim 1, wherein A is a straight-chain $C_{1-7}$alkylene having no carbon atoms optionally replaced.

6. A compound as defined in claim 1, wherein A is selected from the group consisting of propylene, butylene, pentylene, hexylene, propoxylene, butoxylene, and pentoxylene.

7. A compound as defined in claim 1, wherein B is phenyl or cis-1-decenyl.

8. A compound selected from the group consisting of:
  7-phenyl-1-[5-(pyridin-2-yl)-1,3,4-oxadiazol-2-yl]-heptan-1-one;
  6-phenyl-1-[5-(pyridin-2-yl)-1,3,4-oxadiazol-2-yl]-hexan-1-one;
  8-phenyl-1-[5-(pyridin-2-yl)-1,3,4-oxadiazol-2-yl]-octan-1-one;
  9-phenyl-1-[5-(pyridin-2-yl)-1,3,4-oxadiazol-2-yl]-nonan-1-one;
  1-[5-(pyridin-2-yl)-1,3,4-oxadiazol-2-yl]-octadec-9-en-1-one;
  6-phenyl-1-[5-(pyridin-3-yl)-1,3,4-oxadiazol-2-yl]-hexan-1-one;
  7-phenyl-1-[5-(pyridin-3-yl)-1,3,4-oxadiazol-2-yl]-heptan-1-one;
  7-phenyl-1-[5-(pyridin-4-yl)-1,3,4-oxadiazol-2-yl]-heptan-1-one; and
  6-phenoxy-1-(5-pyridin-2-yl-[1,3,4]oxadiazol-2-yl)-hexan-1-one.

* * * * *